United States Patent [19]
Topping et al.

[11] Patent Number: 5,565,076
[45] Date of Patent: Oct. 15, 1996

[54] FLUORIDE SENSING ELECTRODES WITH LONGER SERVICE LIFE, RETROFITTABLE SHIELDS THEREFOR, AND PROCESSES UTILIZING SUCH ELECTRODES

[75] Inventors: Joseph C. Topping, Austin, Tex.; Jeffrey T. Simpson, Rochester Hills, Mich.

[73] Assignee: Henkel Corporation, Plymouth Meeting, Pa.

[21] Appl. No.: 445,634

[22] Filed: May 22, 1995

[51] Int. Cl.$^6$ .................................................. G01N 27/26
[52] U.S. Cl. ...................... 204/419; 204/416; 204/435; 422/82.03
[58] Field of Search .................................. 204/416, 419, 204/435; 422/82.03

[56] References Cited

U.S. PATENT DOCUMENTS

| | | | |
|---|---|---|---|
| Re. 24,222 | 9/1956 | Patnode et al. | 204/416 |
| 3,431,182 | 3/1969 | Frant | 204/1 |
| 4,049,526 | 9/1977 | Maurer | 204/196 |
| 4,128,468 | 12/1978 | Bukamier | 204/195 |
| 5,245,869 | 6/1995 | Noding et al. | 204/416 |
| 5,393,402 | 2/1995 | Dervaes et al. | 204/419 |

OTHER PUBLICATIONS

*Fluorocarbon Elastomers*, vol. 7, pp. 258–267 no month or year available.

*Primary Examiner*—Bruce F. Bell
*Attorney, Agent, or Firm*—Ernest G. Szoke; Wayne C. Jaeschke; Norvell E. Wisdom, Jr.

[57] ABSTRACT

The service life of a conventional free fluoride ion sensitive electrode can be improved by shielding the outer casing of the conventional electrode against contact with the liquid composition in which the free fluoride ions concentration is to be measured, particularly when the solution is a hot acid solution containing surfactants and/or oxidizing agents, such as is normally used for cleaning aluminum beverage containers or providing a protective surface treatment to aluminum surfaces.

20 Claims, 3 Drawing Sheets

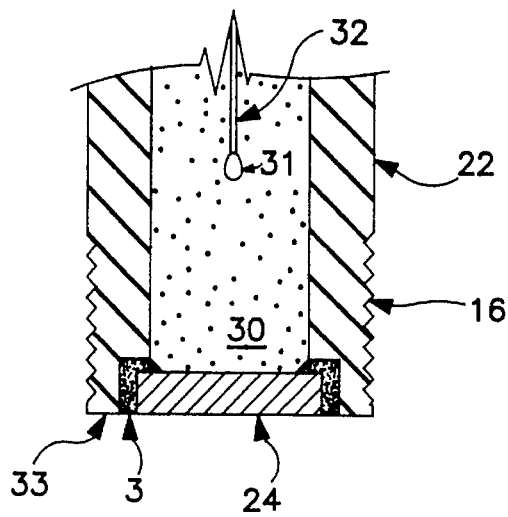
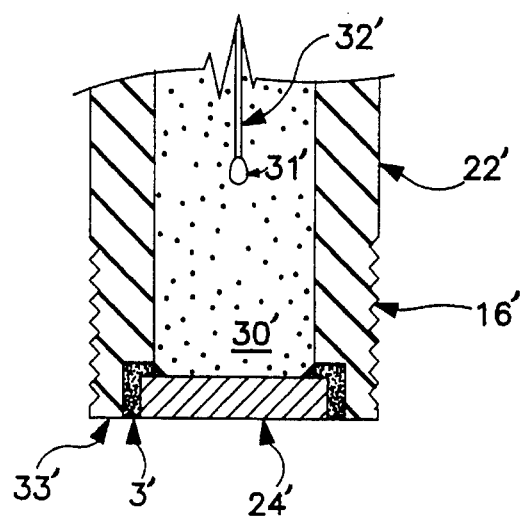
FIG. 2a
FIG. 2b
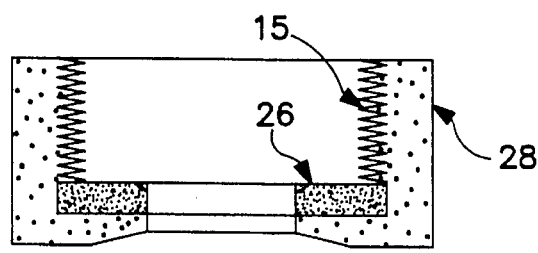
FIG. 3
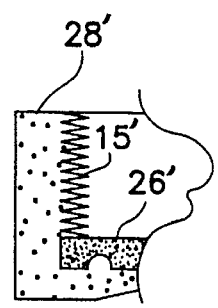
FIG. 3a
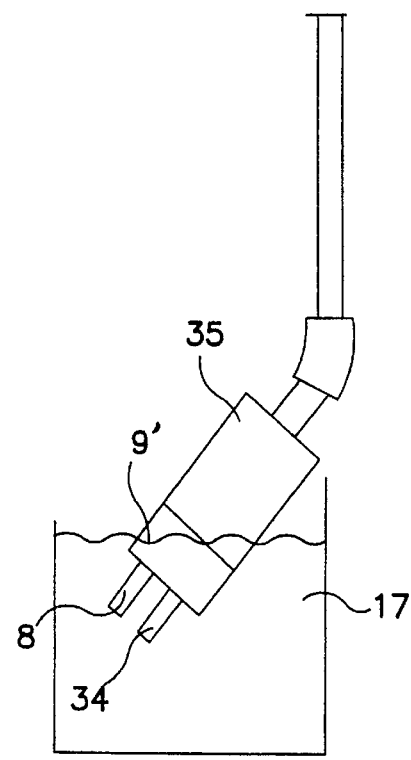
FIG. 5

FLUORIDE SENSING ELECTRODES WITH LONGER SERVICE LIFE, RETROFITTABLE SHIELDS THEREFOR, AND PROCESSES UTILIZING SUCH ELECTRODES

BACKGROUND OF THE INVENTION

1. Field of the Invention

This invention relates to electronic and electrochemical apparatus and methods for measuring the concentration of fluoride ions in aqueous liquid compositions. The general principles of the apparatus are described in U.S. Pat. No. 3,431,182 of Mar. 4, 1969 to Frant, the entire disclosure of which, except to the extent that it may be contrary to any explicit statement herein, is hereby incorporated herein by reference. This invention is more particularly related to modifications that prolong the service life of the electrodes, particularly when the latter are used in contact with hot acidic aqueous compositions containing surfactants and/or oxidizing agents; such compositions are customarily employed in cleaning aluminum beverage containers in a high speed processing line and in forming protective coatings on aluminum surfaces generally.

2. Discussion of Related Art

One of the necessary parts of apparatus according to this invention and the prior art is a substantially liquid impermeable membrane that is constituted of ion-sensitive crystalline fluoride(s). In a complete free fluoride ion sensitive electrode, this membrane is physically arranged to have one surface of the membrane contacted by an ionically conductive liquid in which the concentration of free fluoride ions is to be measured with the aid of the free fluoride ion sensitive electrode. The other side of the membrane is in indirect electrical contact, via physical contact with a first liquid ionic solution of known composition, with a first "reference electrode", i.e., an electrode, such as a silver-silver chloride electrode, that automatically maintains itself at a fixed potential as long as the composition of the ionic solution with which it is in contact does not change and the current density flowing through it is small. The first ionic solution of known composition, the first reference electrode, and the membrane described above are all assembled within and/or on the surface of a container, usually a tubular container, in such a manner that (i) the membrane has one side in contact with the first ionic solution of known composition and its other side on the outside of the container, (ii) the first liquid ionic solution of known composition is sealed within the container, (iii) the first reference electrode is in physical contact with the first liquid ionic solution of known composition and is not in physical contact with the membrane, but is electrically connected thereto via the first liquid ionic solution of known composition; and (iv) the metallic part of the first reference electrode is connected through a metallic electrical conductor lead to the space outside a single sealed space within the container that contains a metallic part of the first reference electrode, the first liquid ionic solution of known composition, and the interior side of the solid fluoride(s) membrane. The Frant reference teaches that the container may be made of any liquid-impervious, substantially rigid, electrically insulating material that is substantially chemically inert to salt solutions containing fluoride ions with which the container might be placed in contact, and in practice most if not all commercially available free fluoride ion sensitive electrodes have plastic containers, usually of poly{phenylene sulfide}, with or without inorganic fillers.

When a free fluoride ion sensitive electrode is in use, the electrical lead from the container for the first reference electrode is connected via a metallic conductor to a low current voltage measuring device and through the latter to a second reference electrode, which may or may not be at the same inherent, self-maintained potential as the first reference electrode. The second reference electrode is in contact with a second liquid ionic solution of known composition, which may or may not be the same as the composition of the first liquid ionic solution, and the second liquid ionic solution is not in physical contact with, but is in indirect electrical contact with, the aqueous composition containing the concentration of free fluoride ions to be measured, the indirect contact being established through one of the devices known in the art, such as a glass fiber, gel of ionic solution, porous TEFLON™ polytetrafluoroethylene plug as described, for example in U.S. Pat. No. 4,128,468 of Dec. 5, 1978 to Bukamier, "flowing junction", or the like, which permits electrical conductance via ion charge transfer while preventing any substantial physical mixing between the second liquid ionic solution of known composition and the liquid in which the concentration of free fluoride ions is to be measured.

Although fluoride sensitive electrodes of this type have been in use for decades, it has been widely recognized in the art that one of their major disadvantages is an instability of performance. Such instability is usually first manifested as a change in the voltage reading that corresponds to a particular value of free fluoride ions, necessitating frequent recalibration of the particular fluoride sensitive electrode used. Eventually, the electrode may become non-responsive to changes in fluoride concentration within the range in which measurement is needed for the process control of the particular solution being monitored with the electrode, so that the electrode must be replaced. This is a substantial source of expense and also of inconvenience and hazard, inasmuch as many of the solutions in which fluoride concentrations are measured contain hazardous ingredients such as hot hydrofluoric acid and the free fluoride ion sensitive electrodes are often mounted in the wall of a container vessel for the process solution being monitored, well below the highest liquid level in the vessel; considerable care must be exercised when replacing any such component in contact with such a solution in order to avoid injury.

Most prior art attempts to improve the life of free fluoride ion sensitive electrodes have been directed to improving the quality of the seal between the solid fluoride(s) membrane and the container wall in which the membrane is fixed, in order to prevent or at least minimize opportunities for fluid and/or electrical leaks through this desirably completely sealed interface. For example, U.S. Pat. No. 4,049,526 of Sep. 20, 1977 to Maurer teaches that a slow setting type of cement is practically required for sealing the solid fluoride(s) membrane to the insulating container, but that such a slow-setting cement has poor long term resistance to many solutions in which measurement of the free fluoride ion concentration with the free fluoride ion sensitive electrode is desired, so that the slow setting cement, even after it is completely set, should be protected from these solutions with a fast setting cyanoacrylate cement shield.

More recently than the issue date of the Maurer patent, extensive use has been made of a VITON™ or like fluorocarbon elastomer O-ring or gasket to protect the integrity of the slow setting cement interface between the solid fluoride(s) membrane and the insulating container wall. The solid fluoride(s) membrane normally is cemented into a recess provided in the insulating container wall, so that the bottom surface of the assembly is a flat circular disk that has the solid fluoride(s) membrane as its center, surrounded by an annular ring of cement which itself is surrounded by an annular ring of the material of which the major insulating part(s) of the container wall are constructed. The exterior of the insulating container wall immediately at and away from this flat circular disk is threaded for a sufficient distance to hold in place a retaining collar, with corresponding female threading on its interior cylindrical surface and a circular hole through its flat surface. The sizes of the circular holes in the retaining collar and in the elastomeric O-ring or gasket are at least slightly smaller than the size of the exposed exterior surface of the solid fluoride(s) membrane, and the exterior diameter of the O-ring or gasket is small enough to fit within the retaining collar and large enough to be retained thereby when the latter is screwed into place over the threaded end of the insulating container exterior, so that the O-ring or gasket is compressed and forms a seal that at least initially is liquid tight. However, neither this nor any other expedient known to prior art has proved to be fully satisfactory for assuring long term reliability for the free fluoride ion sensitive electrodes now in general use.

DESCRIPTION OF THE INVENTION

OBJECTS OF THE INVENTION

One major object of the invention is to prolong the time interval between recalibrations and/or replacements of free fluoride ion sensitive electrodes by providing an improved type of free fluoride ion sensitive electrode. Another object is to provide a retrofittable element or collection of elements to convert free fluoride ion sensitive electrodes of conventional current design into a longer lived type. Another alternative or concurrent object is to improve the operation of processes utilizing free fluoride ion sensitive electrodes by utilizing electrodes of improved design. Other objects will be apparent from the description below.

SUMMARY OF THE INVENTION

It has been discovered that substantial increases in the life of a free fluoride ion sensitive electrode that is otherwise constructed generally according to the prior art can be achieved by providing the exterior surface of the insulating container wall of the free fluoride ion sensitive electrode with a shield of solid material that is impervious to the solution in which the free fluoride ions concentration is to be measured, so that the exterior surface of the container wall of a currently conventional free fluoride ion sensitive electrode is protected against slow deterioration as a result of reaction with the liquid composition in which the free fluoride ions concentration is to be measured. The shield may be in a single piece or in multiple pieces and preferably eliminates and at the very least greatly reduces contact between the exterior surface of the insulating container wall and the solution in which the free fluoride ions concentration is to be measured.

Accordingly, one major embodiment of the invention is a free fluoride ion sensitive electrode, comprising:

(A) a substantially liquid impermeable membrane that is constituted of one or more fluoride ion-sensitive solid, crystalline, substantially water insoluble fluorides;

(B) a container with walls that are electrically insulating, except in a portion of the walls that is constituted exclusively of membrane component (A), with one side of said membrane component on the exterior and the other side of said membrane component on the interior of the container, the walls of the container enclosing a substantially liquid- and vapor-tight space;

(C) a volume of a first liquid ionic solution of known composition and concentration confined within the substantially liquid- and vapor-tight space within container component (B) and in physical contact with the interior surface of membrane component (A);

(D) a first reference electrode enclosed within the substantially liquid- and vapor-tight space within container component (B), said first reference electrode including a metallic electrical conductor that is in physical contact with ionic solution component (C) but is not in physical contact with membrane component (A);

(E) an electrically conducting lead component that is in physical contact with both the metallic electrical conductor part of reference electrode component (D) and a point outside the substantially liquid- and vapor-tight space within container component (B) but is not in physical contact with membrane component (A) or with component (C); and (F) shield means including an exterior surface that prevents any substantial physical contact between (i) any liquid composition in which the concentration of free fluoride ions is to be measured with the aid of the free fluoride ion sensitive electrode and (ii) any part of the exterior wall of container component (B) other than a part of said exterior wall which is constituted exclusively by one side of membrane component (A), while allowing physical contact between (i) any liquid composition in which the concentration of free fluoride ions is to be measured with the aid of the free fluoride ion sensitive electrode and (ii) at least part of the exterior surface of membrane component (A).

All of these components except shield means (F) are conventional per se. Accordingly, another major embodiment of the invention is a retrofittable shield means for converting a conventional free fluoride ion sensitive electrode having components (A) through (E) as recited above into a free fluoride ion sensitive electrode according to this invention, in which the walls of the container for the first reference electrode are protected from contact with the liquid in which the free fluoride ion(s) concentration is to be measured, except in a part of the wall constituted exclusively of membrane component (A) as described above.

Still another major embodiment of the invention is a process comprising steps of (i) monitoring the free fluoride ions concentration of a reactive process liquid as the process liquid is used by measuring the voltage developed between a free fluoride ion sensitive electrode and a second reference electrode when both these electrodes are in electrical contact with the process liquid and (ii) adjusting the free fluoride ions concentration of the process liquid when necessary to maintain said concentration between preselected limits, wherein an electrode according to the invention as described above is used as the free fluoride ion sensitive electrode.

BRIEF DESCRIPTION OF THE DRAWINGS

FIG. 2a is a more detailed view, entirely in section, of the end of the embodiment shown in FIG. 1 which includes the solid fluoride(s) membrane, before the retaining collar and flat gasket seal are put into place; these latter components are shown in section in FIG. 3, which has approximately the same scale as FIG. 2. FIG. 3a is a view of the left part only of an alternative embodiment of FIG. 3, in which the retaining surface includes an annular projection, shown in cross section in FIG. 3a, to focus compressive force into a particular portion of an elastomeric body against which it is compressed. FIG. 2b, which is the same as FIG. 2a except that the reference numbers are primed, shows the details of the end portion of the embodiment shown in FIG. 4 in the same manner as FIG. 2a shows the details of the end portion of the embodiment shown in FIG. 1. FIG. 5 is a projection view of additional parts of one embodiment of overall process apparatus into which the parts of the apparatus shown in greater detail in FIGS. 1–4 may be incorporated. In all of these drawings, like components are indicated by like reference numbers.

DETAILED DESCRIPTION OF THE INVENTION, INCLUDING PREFERRED EMBODIMENTS

Figure 1:
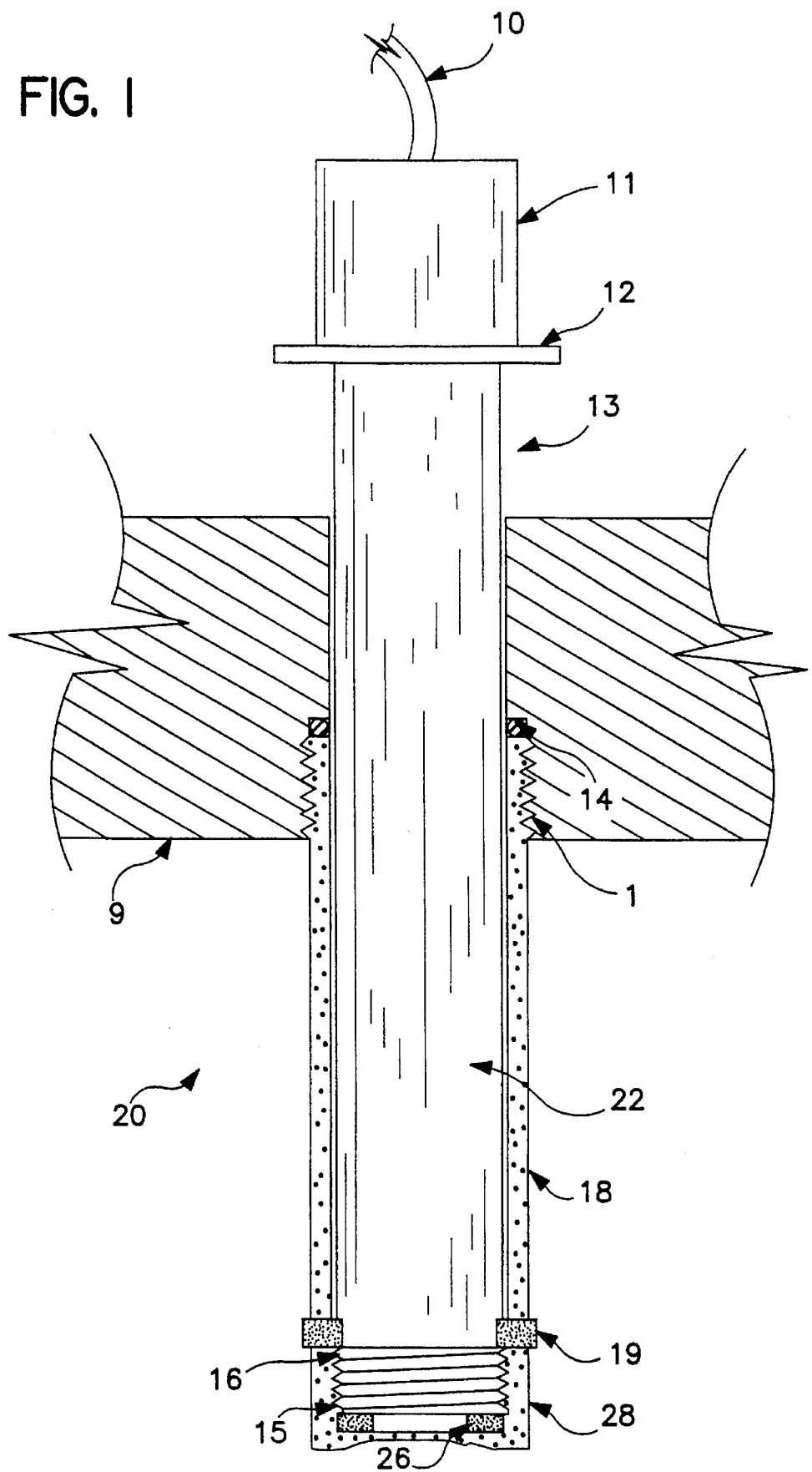
FIG. 1 is a general overview, partly in projection and partly in section, of one preferred embodiment of the invention, particularly suitable for construction by retrofitting a currently common commercial type of free fluoride ion sensitive electrode.

The shield means may be constructed of one or more materials which are impervious to and chemically unreactive toward the liquid in which the free fluoride ions concentration is to be measured with apparatus according to this invention, and a wide variety of possible designs have been contemplated. For example, a very simple single piece shield may be made from a cylindrical shaped balloon-like elastomer sac with one completely open end and an opposite end which is closed except that it includes a small central hole, preferably a hole with a reinforced rim that projects at least slightly on at least its interior side. Such an elastomer sac can be stretched over the end of a conventional free fluoride ion sensitive electrode such as is depicted in FIG. 2a, with or without a threaded end, and tensioned from above so that the hole in the lower end of the sac forms a seal against the surface of the membrane 24. In a process tank open to the atmosphere, the sides of the sac are simply made long enough to reach above the level of the liquid in which the fluoride ions concentration is to be measured, and may be secured by any convenient means. Instead of a simple sac, a shield with a bellows-like wall and a bottom fitting of elastomer with a small central hole therein can also be used in an otherwise similar manner.

Any elastomeric component of the shield that is likely to come into contact with a hot aqueous liquid containing fluoride ions and/or oxidizing agents or surfactants, such as the most commonly practically used liquids in which a free fluoride ions concentration is to be measured, most preferably is made of elastomer that is a copolymer of tetrafluoroethylene and perfluoro(methylvinylether), commercially available under the trade name KALREZ. Next most preferred are other commercially available fluorocarbon elastomers such as (i) copolymers of vinylidene fluoride and hexafluoropropylene and terpolymers of vinylidene fluoride, tetrafluoroethylene, and hexafluoropropylene, both available under the trademarks DAI-EL, FLUOREL, TECHNOFLON, and VITON from Diakin, 3M, Montedison, and DuPont respectively and (ii) copolymers of vinylidene fluoride and chlorotrifluoroethylene, available under the trademark KEL-F from 3M. If only less potentially damaging liquids than those noted above are to be tested for free fluoride ions concentrations with a shielded free fluoride ion sensitive electrode according to the invention, less expensive elastomers than these may be equally suitable.

In many cases, free fluoride ion sensitive electrodes are now utilized in a liquid tight mounting or housing, with a fluoride sensitive membrane and most or all of the other parts of the free fluoride ion sensitive electrode located well below the highest level of liquid in which the fluoride ions concentration is to be measured with the free fluoride ion sensitive electrode. In such cases, particularly when it is desired to change existing equipment as little as is feasible while converting to a shielded free fluoride ion sensitive electrode according to this invention, a shield means incorporating some rigid material(s) as well as at least one elastomeric one is generally preferred. The term "rigid" in this context means primarily that the material so described is capable of transmitting a compressive force to the elastomeric material also used in the shield means, without itself being substantially compressed. In quantitative terms, when a material is described as "rigid" and is used in a shield means along with another material described as "elastomeric" or as an "elastomer", "rigid" means that, when the elastomeric material is compressed against the rigid one by a compressive force, the percentage reduction in thickness of the elastomeric material is least 2, and, with increasing preference in the order given, preferably is at least 3, 5, 1 0, 20, 30, or 50, times the percentage reduction in thickness of the rigid material.

When screw threading is to be relied on, either directly or indirectly by virtue of a compressive force exerted by a screwed joint on an elastomeric gasket or the like, to provide a liquid tight seal in a free fluoride ion sensitive electrode apparatus according to this invention, it is generally preferable for at least one side of the threaded connection to be constructed of a strong metal, because such threaded joints are generally more reliable than those in which both sides of the screw threads in a joint are constructed of some weaker material such as plastic. For this reason, when a design such as is shown in FIG. 1 is used, the collar preferably is metal rather than the plastic that was taught to be preferable by Frant, because the container wall in current commercially available free fluoride ion sensitive electrodes almost always is plastic. (The electrical shielding effect of a metal conductor may also contribute some beneficial effect to the shield means.) The single most preferred metallic material for the shield means is austenitic stainless steel, a variety of which are readily available commercially under "Type" numbers that consist of three digits of which the first digit is 3, and possibly of some letters also, such as Types 304, 316, and 316L stainless steels. However, any other metal with adequate mechanical strength, machinability, and chemical corrosion resistance is entirely adequate.

In the most common currently conventional type of free fluoride ion sensitive electrode, component (B) is substantially cylindrical and its exterior walls comprise an elongated lateral section connected on one end thereof to a working end section, and the working end section comprises (i) a central portion that is constituted entirely of exterior surface of membrane component (A), (ii) an exterior portion that is integral with the nearest parts of the elongated lateral section of container component (B), and (iii) an intermediate portion that is the exterior part of a volume of completely set, originally slow-setting, cement that bonds membrane component (A) to the exterior portion of the working end section. For this type of currently available commercial free fluoride ion sensitive electrodes, a preferred type of retrofittable shield means comprises:

(1) a primary elastomeric shield body having a central hole therethrough and having shape, dimensions, and elastic properties such that the primary elastomeric shield body can be compressed, without causing mechanical damage to any part of any of components (A) through (E) of the electrode to be retrofitted, sufficiently tightly against the working end section of container component (B) so that the primary elastomeric shield body forms, without obstructing access to all of the central portion of the working end section of component (B), a sealing contact between itself and a sufficient area of the working end section of container component (B), so that (i) the sealing contact prevents any flow of liquid, between said primary elastomeric shield body and said working end section of container component (B), to a point where the liquid would contact any part of the exterior walls of container component (B) that is not constituted exclusively of exterior surface of membrane component (A) and (ii) any area of said working end section of container component (B) that is interior to the sealing contact formed thereagainst consists exclusively of exterior surface of membrane component (A);

(2) a rigid shield body, which may be either a single piece or a subassembly of a plurality of rigid shield elements connected by gasketing, adhesive, or a like material, said rigid shield body having a size and shape such that it can fit over all otherwise uncovered parts of the walls of container component (B) except for at least one part thereof which is constituted exclusively of said central portion of said working end section of container component (B); said rigid shield body also having on one end thereof an interior retaining surface including a hole therethrough, said interior retaining surface being adapted in size and shape to cause retention of said primary elastomeric shield body when pressed thereagainst and being a surface of a portion of the rigid shield body which is sufficiently strong and rigid to transmit to the primary elastomeric shield body when pressed thereagainst, without itself being substantially compressed and without causing mechanical damage to any part of components (A) through (E) of the electrode to be retrofitted, a compressive force that causes the primary elastomeric shield body to form a liquid-tight seal between a sufficient area of itself and a sufficient area of the interior retaining surface of the rigid shield body to prevent any flow of liquid, between the primary elastomeric shield body and the interior retaining surface, to a point where the liquid would contact any part of the exterior walls of container component (B), except possibly for one or more parts thereof each of which is constituted exclusively of exterior surface of membrane component (A); and (3) means for maintaining alignment among the primary elastomeric shield body, the interior retaining surface of the rigid shield body, and the working end section of the exterior walls of container component (B) and for maintaining compressive force between the interior retaining surface of the rigid shield body and the working end section of the exterior walls of container component (B), without causing mechanical damage to any part of any of components (A) through (E), so as to form from the rigid shield body, the primary elastomeric shield body, and the container component (B) an assembly in which (i) the primary elastomeric shield body is between the interior retaining surface of the rigid shield body and the working end section of the exterior walls of container component (B) and is suitably compressed so as to form a sealing contact, between the primary elastomeric shield body and a sufficient area of each of the interior retaining surface of the rigid shield body and the working end section of the exterior walls of container component (B), so that (i) the sealing contact prevents any flow of liquid, between the primary elastomeric shield body and either of the interior retaining surface of the rigid shield body or the working end section of the exterior walls of container (B), to a point where the liquid would contact any part of the exterior walls of container component (B), except possibly for one or more parts thereof each of which is constituted exclusively of exterior surface of membrane component (A); (ii) any area of said working end section of container component (B) that is interior to the sealing contact formed thereagainst by the primary elastomeric shield body consists exclusively of exterior surface of membrane component (A); and (iii) there exists at least a part of the exterior surface of membrane component (A) in the working end section of container component (B) that is not prevented by any part of the shield means from making physical contact with any liquid with which any portion of the assembly of the rigid shield body, the primary elastomeric shield body, and container component (B) that includes said working end section of container component (B) is brought into contact. In a closely related preferred embodiment of a complete free fluoride ion sensitive electrode according to the invention, (I) the exterior walls of container component (B) comprise an elongated section connected on one end thereof to a working end section, and the working end section comprises (i) a central portion that is constituted entirely of exterior surface of membrane component (A), (ii) an exterior portion that is integral with the nearest parts of the elongated lateral section of container component (B), and (iii) an intermediate portion that is the exterior part of a volume of completely set, originally slow-setting, cement that bonds membrane component (A) to the exterior portion of the working end section; and (II) the shield means (F) comprise:

(II.1) a primary elastomeric shield body having a central hole there-through and having shape, dimensions, and elastic properties such that the primary elastomeric shield body can be compressed, without causing mechanical damage to any part of any of components (A) through (F) of the electrode, sufficiently tightly against the working end section of the walls of container component (B) recited in part (I) above, so that (i) the sealing contact prevents any flow of liquid, between said primary elastomeric shield body and said working end section of container component (B), to a point where the liquid would contact any part of the exterior walls of container component (B) that is not constituted exclusively of exterior surface of membrane component (A) and (ii) any area of said working end section of container component (B) that is interior to the sealing contact formed thereagainst consists exclusively of exterior surface of membrane component (A);

(II.2) a rigid shield body, which may be either a single piece or a subassembly of a plurality of rigid shield elements connected by gasketing, adhesive, or a like material, said rigid shield body having a size and shape such that it can fit over all otherwise uncovered parts of the walls of container component (B) except for at least one part thereof which is constituted exclusively of said central portion of said working end section of container component (B); said rigid shield body also having on one end thereof an interior retaining surface including a hole therethrough, said interior retaining surface being adapted in size and shape to cause retention of said primary elastomeric shield body when pressed thereagainst and being a surface of a portion of the rigid shield body which is sufficiently strong and rigid to transmit to the primary elastomeric shield body when pressed thereagainst, without itself being substantially compressed and without causing mechanical damage to any part of components (A) through (F) of the electrode, a compressive force that causes the primary elastomeric shield body to form a liquid-tight seal between a sufficient area of itself and a sufficient area of the interior retaining surface of the rigid shield body to prevent any flow of liquid, between the primary elastomeric shield body and the interior retaining surface, to a point where the liquid would contact any part of the exterior walls of container component (B), except possibly for one or more parts thereof each of which is constituted exclusively of exterior surface of membrane component (A); and (II.3) means for maintaining alignment among the primary elastomeric shield body, the interior retaining surface of the rigid shield body, and the working end section of the exterior walls of container component (B) and for maintaining compressive force between the interior retaining surface of the rigid shield body and the working end section of the exterior walls of container component (B), without causing mechanical damage to any part of any of components (A) through (E), so as to form from the rigid shield body, the primary elastomeric shield body, and the container component (B) an assembly in which (i) the primary elastomeric shield body is between the interior retaining surface of the rigid shield body and the working end section of the exterior walls of container component (B) and is suitably compressed so as to form a sealing contact, between the primary elastomeric shield body and a sufficient area of each of the interior retaining surface of the rigid shield body and the working end section of the exterior walls of container component (B), so that (i) the sealing contact prevents any flow of liquid, between the primary elastomeric shield body and either of the interior retaining surface of the rigid shield body or the working end section of the exterior walls of container (B), to a point where the liquid would contact any part of the exterior walls of container component (B), except possibly for one or more parts thereof each of which is constituted exclusively of exterior surface of membrane component (A); (ii) any area of said working end section of container component (B) that is interior to the sealing contact formed thereagainst by the primary elastomeric shield body consists exclusively of exterior surface of membrane component (A); and (iii) there exists at least a part of the exterior surface of membrane component (A) in the working end section of container component (B) that is not prevented by any part of the shield means from making physical contact with any liquid with which any portion of the assembly of the rigid shield body, the primary elastomeric shield body, and container component (B) that includes said working end section of container component (B) is brought into contact.

More preferably, in a complete free fluoride ion sensitive electrode according to this invention, whether constructed originally according to the invention or formed by retrofitting an existing unshielded or incompletely shielded free fluoride ion sensitivie electrode: (i) component (B) and the shield body have shapes that are substantially those of hollow cylinders and have lateral exterior and interior substantially cylindrical surfaces that are longer than the diameter of their substantially flat end surfaces; (ii) the the interior retaining surface of the shield body is a substantially flat annular disk; (iii) the primary elastomeric shield body is a fluorocarbon elastomer gasket; and (iv) the means for maintaining alignment and compressive force comprise (iv.1) male screw threads on a threaded zone of the lateral substantially cylindrical exterior wall of container component (B), this threaded zone extending to the end of said exterior wall adjacent to the working end section of the exterior wall, (iv.2) a substantially cylindrical unthreaded zone of the interior lateral substantially cylindrical surface of the single piece rigid shield body, or of a terminal rigid shield element of the rigid shield body subassembly if the rigid shield body is a subassembly, immediately adjacent to the interior retaining surface thereof; (iv.3) a cylindrical volume, of which said unthreaded zone forms the outer lateral walls, within the rigid shield body, this cylindrical volume being wide and long enough to accommodate the fluorocarbon elastomer gasket in an uncompressed condition, (iv.4) a substantially cylindrical female threaded zone of the interior lateral substantially cylindrical surface of the single rigid shield body, or of a terminal rigid shield element of the shield body subassembly if the shield body is a subassembly, immediately adjacent to the unthreaded zone recited in part (iv.2) on the opposite side thereof from the interior retaining surface, said female threaded zone being adapted to mate with the male screw threads recited in part (iv.1) and having an inside diameter smaller than the outside diameter of the fluorocarbon elastomer gasket in its uncompressed state; (v) the compressibility of the fluorocarbon elastomer gasket and the relative sizes of the fluorocarbon elastomer gasket and of the elements recited in parts (iv.1) through (iv.4) are such that the fluorocarbon elastomer gasket can be compressed, without causing mechanical damage to any other part of any of components (A) through (F), by mating some or all of the female threaded zone of the interior lateral substantially cylindrical surface of the single rigid shield body, or of a terminal rigid shield element of the shield body subassembly if the shield body is a subassembly, while the fluorocarbon elastomer gasket is in place between the female threaded zone and the interior retaining surface, with some or all of the male screw threads recited in part (iv.1), to a sufficient degree to form a sealing contact between said fluorocarbon elastomer gasket and a sufficient portion of each of said interior retaining surface and said working end section of the exterior walls of container component (B) that will prevent any flow of liquid, between (v.1) said primary elastomeric shield body and (v.2) either of (v.2.1) said interior retaining surface of the rigid shield body or a terminal element thereof or (v.2.2) said working end section of the exterior walls of container (B), to a point where the liquid would contact any part of the exterior walls of container component (B), except possibly for one or more parts thereof each of which is constituted exclusively of exterior surface of membrane component (A).

In one particularly preferred embodiment of the preferred embodiment described immediately above: (i) the rigid shield body is a subassembly of at least two rigid shield elements and at least one elastomeric gasket in addition to the above-recited primary elastomeric shield body; (ii) one of the rigid shield elements is a terminal collar element comprising the elements recited in parts (iv.2) and (iv.3) of the immediately preceding paragraph; (iii) all of the rigid shield elements except the terminal collar element are hollow cylinders with an inside diameter sufficiently large that they can pass freely over the outer lateral walls of container component (B) and have both internal and external lateral surfaces that are substantially cylindrical in shape, except that one end of the exterior surface of a non-terminal shield element which includes the end among all ends of all the non-terminal rigid shield elements that is farthest from the terminal collar element when the collar element and all the non-terminal rigid shield elements are assembled in the shield body subassembly in a configuration intended for use, has a zone of male screw threads thereon, (iv) the free fluoride ion sensitive electrode is mounted on and through a solid mounting block having boundaries including two substantially flat and parallel surfaces, said mounting block having a substantially cylindrical hole therethrough that is bounded by a substantially cylindrical lateral interior surface of the mounting block and has a sufficiently large diameter that the end of the elongated portion of the exterior walls of container component (B) opposite the working end section thereof can slide freely through said hole through the mounting block, (v) the lateral internal surface of the mounting block that bounds said hole through the mounting block has, on the end thereof that is nearer to the shield body when assembled, a female threaded zone suitable to mate with the zone of male screw threads recited in part (iii), (vi) the elongated portion of the exterior walls of container element (B) is sufficiently long to extend through the entire thickness of the mounting block when assembled, and is rigidly attached, on the side of the mounting block opposite the rigid shield subassembly, to a projection sufficiently large in size that the projection can not pass through the hole in the mounting block through which the elongated portion of the exterior walls of container element (B) passes; (vii) means, preferably a coil spring, for exerting a compressive force between the projection recited in part (vi) and the flat surface of the mounting block nearer to said projection are present; (viii) an elastomeric gasket is present between (viii.1) the end of the terminal collar rigid shield element farther from the internal retaining surface therein and (viii.2) the nearer end of the only other rigid shield element, if there is only one, or the nearer end of the nearer or nearest of the other rigid shield elements if there is more than one such element, and, if there is more than one rigid shield element other than the terminal collar element, an elastomeric gasket is also present between each additional end, other than the end having a zone of male screw threads thereon, of a nonterminal rigid shield element and the nearer or nearest end of another distinct nonterminal rigid shield element; (ix) each of the gaskets recited in part (viii) above that is present has (ix.1) a hole therethrough, this hole being large enough that the cylindrical exterior walls of container component (B) can slide freely therethrough, and (ix.2) an external size, external surface shape, and elastomeric properties such that (ix.2.1) the gasket when suitably compressed will form a sealing interface between itself and each rigid surface with which it is in contact, so that no liquid can flow through the interface between the gasket and the surface of either rigid shield element with which it is in contact to a point where such liquid would contact any part of the exterior walls of container component (B) that is not constituted exclusively of exterior surface of membrane component (A) and (ix.2.2) the gasket can be suitably compressed as recited in part (ix.2.1) without requiring a compressive force large enough to cause mechanical damage to any other part of the free fluoride ion sensitive electrode or the mounting block; (x) a sufficient part of the female threaded zone on the interior of the terminal collar rigid shield element is mated, while the fluorocarbon elastomer gasket that constitutes the primary elastomeric shield body is in place between the female threaded zone of the terminal collar rigid shield element and the interior retaining surface of the terminal collar rigid shield element, with some or all of the male screw threads recited in part (iv.1) of the immediately preceding paragraph, without causing mechanical damage to any part of any of components (A) through (F), to a sufficient degree to form a sealing contact between said fluorocarbon elastomer gasket and a sufficient portion of each of the interior retaining surface of the terminal collar rigid shield element and the working end section of the exterior walls of container component (B) that will prevent any flow of liquid between said elprimary elastomeric shield body and either of said interior retaining surface of said shield body or said working end section of the exterior walls of container (B) to a point where the liquid would contact any part of the exterior walls of container component (B), except for one or more parts thereof each of which is constituted exclusively of exterior surface of membrane component (A); and (xi) a compressive force is applied between (xi.1) the projection attached to the part of the elongated exterior surface of the walls of container component (B) farther from the exterior surface of membrane component (A) and (xi.2) the nearer flat surface of the mounting block, said compressive force being sufficient to compress each gasket suitably as recited in part (ix.2.1) above and insufficient to cause any mechanical damage to any part of the free fluoride ion sensitive electrode or the mounting block.

More preferably in this embodiment in which the shield body includes a subassembly of at least two rigid shield elements, (i) the nonlateral surface of the rigid shield element that is adjacent to the lateral surface of the rigid shield element that has male threads thereon is substantially flat; (ii) the hole through the mounting block through which the elongated exterior wall of container component (B) passes includes an unthreaded cylindrical zone adjacent to its female threaded zone and a substantially flat retaining surface adjacent to said unthreaded cylindrical zone on the end thereof opposite the female threaded zone of the hole; and (iii) an upper fluorocarbon elastomer gasket is present in the space bounded by the cylindrical walls of said unthreaded cylindrical zone, said flat nonlateral surface of the rigid shield element, and the substantially flat retaining surface in the hole in the mounting block through which the elongated exterior wall of container component (B) passes, so that said upper fluorocarbon elastomer gasket will be compressed along with the other gaskets recited in the paragraph immediately above, the upper fluorocarbon elastomer gasket having (iii.1) an inside diameter through which the elongated portion of the exterior wall of container component (B) can slide freely and (iii.2) an external size, external surface shape, and elastomeric properties such that (iii.2.1) the gasket when suitably compressed will form a sealing interface between itself and each rigid surface with which it is in contact, so that no liquid can flow through the interface to a point where such liquid would contact any part of the exterior walls of container component (B) that is not constituted exclusively of exterior surface of membrane component (A) and (iii.2.2) the gasket can be suitably compressed as recited in part (iii.2.1) by the same compressive force as is used to suitably compress the gaskets as recited in part (ix.2.1) of the immediately preceding paragraph.

In another alternative particularly preferred embodiment of a free fluoride ion sensitive electrode according to this invention as described in the third next paragraph above, (i) the shield body comprises a single rigid shield element having exterior walls that include two nonlateral end portions and an elongated lateral cylindrical portion; (ii) the free fluoride ion sensitive electrode is mounted on and through a solid mounting block having (ii.1) a hole therethrough with a sufficient inside diameter that the elongated cylindrical lateral exterior wall of the single rigid shield element can slide freely therethrough and (ii.2) two substantially flat and parallel boundary surfaces; (iii) the elongated cylindrical lateral exterior wall of the single rigid shield element extends on both sides of the above recited hole in the mounting block; (iv) an annular second elastomeric body (iv.1) is present on the flat surface of the mounting block that is farther from the exterior surface of membrane component (A) and (iv.2) surrounds a zone of the elongated cylindrical lateral exterior wall of the single rigid shield element that projects away from the flat surface of the mounting block that is further from the exterior surface of membrane component (A), said annular second elastomeric body having an inside diameter sufficiently large that the elongated cylindrical lateral exterior wall of the single rigid shield element can slide freely therethrough; (v) a rigid annular compression collar is present in contact with the second elastomeric body on the side thereof opposite the mounting block; and (vi) means for exerting compressive force between the compression collar and the nearer thereto of the flat surfaces of the mounting block are present; (vii) the compressibility of the second elastomeric body and the relative sizes of the second elastomeric body and of the elongated cylindrical lateral exterior wall of the single rigid shield element are such that the second elastomeric body can be compressed, by a compression force that is not large enough to cause mechanical damage to any part of the free fluoride ion sensitive electrode or the mounting block, to a sufficient degree to form a sealing contact, between the second elastomeric body and a sufficient portion of the elongated cylindrical lateral exterior wall of the single rigid shield element, that will prevent any flow of liquid between said second elastomeric body and the elongated cylindrical lateral exterior wall of the single rigid shield element, to a point where the liquid would contact any part of the exterior walls of container component (B), except possibly for one or more parts thereof each of which is constituted exclusively of exterior surfaceface of membrane component (A); and (viii) a compression force as recited in part (vii) is applied by the compression means recited in part (vi); and, optionally, (ix) a spacer ring is present between the exterior walls of container component (B) and the inner walls of the single rigid shield element at a point in space distant from the mating screw contact surfaces of the exterior walls of container component (B) and the inner walls of the single rigid shield element, to maintain the exterior walls of container component (B) and the inner walls of the single rigid shield element in substantially parallel alignment.

Still more preferably in the embodiment described in the immediately preceding paragraph, a spacer ring as recited above is present and forms a seal between itself and both the exterior walls of container component (B) and the inner walls of the single rigid shield element, so as to prevent any flow of liquid, between said spacer and either the elongated cylindrical lateral exterior wall of the single rigid shield element or the cylindrical outer lateral surface of the exterior wall of container component (B), to a point where the liquid would contact any part of the exterior walls of container component (B), except possibly for one or more parts thereof each of which is constituted exclusively of exterior surface of membrane component (A).

Ordinarily, for reasons of simplicity and consequent economy and to minimize the likelihood of any deterioration of the outer surface of container component (B), it is preferable for any space between the outer surface of container component (B) and a shield therefor according to this invention to contain only gas, at substantially the same pressure as that of the environment around but exterior to the shield, rather than any liquid. However, it is advantageous in certain cases, particularly when the pressure in the environment around but exterior to the shield is substantially higher than normal atmospheric pressure, to provide means for controlling the pressure within any space between the outer surface of container component (B) and a shield therefor according to this invention to assure a slightly higher pressure in this space than in the environment around but exterior to the shield, in order to minimize the likelihood of leakage of liquid in which the free fluoride ions concentration is to be measured into the space between the outer surface of container component (B) and a shield therefor according to this invention. If the space is thus pressurized, the presence of liquid in this space can be advantageous, to permit the easy transmission of hydraulic pressure through the liquid.

It is also possible to include an ionic conducting liquid and a second reference electrode, as is taught for an unshielded electrode by the Bukamier patent already noted above, in the space between the outer surface of container component (B) and a shield therefor according to this invention. Ordinarily such an arrangement is unpreferred, inasmuch as it is believed that almost any liquid is more likely to compromise the barrier properties of the outer wall of container component (B) than is air or any chemically non-reactive gas that might alternatively be present in any space between the outer surface of container component (B) and a shield therefor according to this invention. However, such an arrangement would be suitable for extremely confined spaces, in which it is desired to measure free fluoride ions concentrations.

These preferred features are illustrated in specific instances in the drawings. FIG. 1 shows predominantly external features and a few internal features of one preferred assembled free fluoride ion sensitive electrode 20, including a shield according to the invention. The exterior of container wall 22, with its threaded lower end, is shown in projection inside collar 28, shield element 18, gasket 26 which constitutes a primary elastomeric shield body as described above, and mounting block 9, all of these features except the container wall being shown in section in FIG. 1. The mounting block preferably includes another aperture hole to accommodate the second reference electrode, which is conventional and not shown in detail in the figures, and if the liquid composition in which the free fluoride ions concentration is to be measured is subject to substantial temperature variations during measurement, the mounting block preferably includes a third aperture hole to accommodate a temperature measuring device, usually a resistance temperature detector or a thermocouple, that will produce a signal when the temperature varies; preferably this signal is an electrical signal that can be connected to conventional means for automatically adjusting the function by which the output voltage generated between the first and second reference electrodes is converted to a value of free fluoride ions concentration, so that the conversion will remain correct even if the temperature of the liquid composition in which the free fluoride ions concentration is to be measured varies substantially. All these temperature correcting means, along with the voltage sensing means and means for converting the voltage to a free fluoride ions concentration value are known in the art and are not considered further herein.

In the particular preferred embodiment shown in FIG. 1, rigid shield element 18 is threaded on its upper end as shown in FIG. 1 and is screwed into a mating internally threaded hole provided in mounting block 15. An optional upper gasket 14 preferably forms a liquid tight seal by compression between the upper end of shield element 18 and the upper end of the hole in mounting block 9, which has a recessed space to accommodate the upper gasket if the latter is used. Upper gasket 14 when used must have an inside diameter that is large enough to avoid substantially impeding sliding motion of container wall 22 through upper gasket 14. (As already briefly noted above, all the parts below and including the bottom of mounting block 9 as shown in FIG. 1 are often immersed in the liquid composition 17 in which the free fluoride ions concentration is to be measured as shown in FIG. 5; in such a mounting, the upper side of mounting block 9 and the portions of the electrode assembly shown above the mounting block in FIG. 1 are normally protected within a liquid-tight housing 35 as known in the art and shown generally in FIG. 5. With such a mounting, the threaded area at the top of shield element 18 which is screwed into mating threads in block 9 is subject to hydrostatic pressure. Because block 9 is usually made of plastic and shield element 18 is usually made of metal, these screw threads often fail to form a liquid-tight seal, particularly if subject to thermal cycling. This is the primary reason for using upper gasket 14. If the bottom of mounting block 9 of the electrode assembly shown in FIG. 1 is mounted entirely above the liquid composition in which the fluoride ions concentration is to be measured and is not otherwise in contact with any liquid under normal use, upper gasket 14 could be omitted.)

Also shown in FIG. 5 is a second reference electrode 34 mounted in the same mounting block as the shielded free fluoride ion sensitive electrode according to this invention.

Above its threaded portion, the hole through the mounting block as shown in FIG. 1 is slightly narrower than below its threaded portion, in order to provide a projection against which the upper gasket can be compressed, but the hole through the mounting block is still large enough that the container wall 22 can slide freely through this hole, in a direction which is up-and-down in FIG. 1. Similarly, the interior diameter of shield element 18 is sufficiently large that container wall 22 can slide freely through it. The force to compress lower gasket 19 and upper gasket 14 is provided by the coil spring 13 shown in FIG. 1. Spring 13 also has a sufficiently large inside diameter that container wall 22 can move freely through it, and it has a sufficiently large outside diameter that it can not pass through the hole in mounting block 9 which accommodates container wall 22. Spring 13 also has a sufficiently large outside diameter that it can not move past optional but preferred flat washer 12 placed between the spring and electrode assembly cap 11, or if no washer is used, past cap 11 itself. Either the cap or the flat washer must be strongly attached to container wall 22, so that the tensioning means can maintain sufficient tension between one of them and the top of mounting block 9. This tension is transmitted by container wall 22 to collar 28, which is the terminal element of the rigid shield for this embodiment and is screwed onto the lower end of container wall 22, so that the upper end of collar 28 compresses gasket 19 against the lower end of rigid shield element 18 to form a liquid tight seal between shield element 18 and collar 28 when assembled and in use. Thus, no liquid from the composition in which at least the lower end of the assembly shown in FIG. 1 is immersed during use can flow into the space between shield member 18 and container wall 22, and the latter is protected from any deterioration that would otherwise result from chemical interactions between container wall 22 and the liquid composition in which the free fluoride ions concentration is to be measured.

The configuration shown in FIG. 1 deliberately provides no firm attachment point between container wall 22 and shield member 18. This prevents the development of longitudinal stresses between these two components of the apparatus that might otherwise be expected to arise from temperature changes, because the shield element and the container wall normally have quite different coefficients of thermal expansion. The inside diameters that are noted above as being sufficiently large to permit free sliding motion therethrough should be selected so as to provide such free sliding motion at all temperatures of anticipated use of the apparatus.

Component 10 of FIG. 1 is a coaxial shielded insulated electrical lead, the central conducting part of which is physically and electrically connected to the metallic part of the first reference electrode. Cap 11 is conventional in the art and should be internally fitted so as to form a substantially liquid and vapor tight seal over the upper end of container wall 22, while permitting passage of an electrical lead therethrough, in order to prevent changes in the composition of first electrolyte of known composition 30 (shown in FIG. 2a).

FIGS. 2a and 3 show important details of the construction of the working end section of the free fluoride ion sensitive electrode 20 which are conventional per se. Solid fluoride(s) membrane 24, which does not show in FIG. 1 because it is hidden by container wall 22, is attached to container wall 22 by a set cement ring 3. Suitable and preferred materials for this cement, for example an epoxy resin, are known in the art. In the particular embodiment shown in FIG. 2a, the first reference electrode is a silver-saturated silver chloride electrode, so that the lower metallic element 32 of the first reference electrode is a silver wire, which is in intimate physical contact with a small body 31 of solid silver chloride, and both are in physical contact with first liquid ionic solution of known composition 30, in this case a saturated solution of silver chloride in water. Exterior threads 16 on the flat lower end 33 of container wall 22 mate with internal threads 15 on collar 28, so that, as collar 28 is screwed onto container wall 22 during assembly before use, lower gasket 26 is compressed against solid fluoride(s) membrane 24, flat end 33 of container wall 22, and set cement ring 3, completely covering the latter and thereby protecting it from contact with the liquid composition in which the free fluoride ions concentration is to be measured during use of the apparatus according to the invention.

One model of commercially available free fluoride ion sensitive electrode already includes elements 3, 33, 30, 24, 16, 22, 31, 32, 26, 15, 28, 10, 11, and 12 from FIGS. 1, 2a, and 3 and is often mounted in a mounting block before use.

This model can therefore be converted to a shielded free fluoride ion sensitive electrode according to this invention by adding elements 18, 19, 1, and 14 as shown in FIG. 1.

Figure 4:
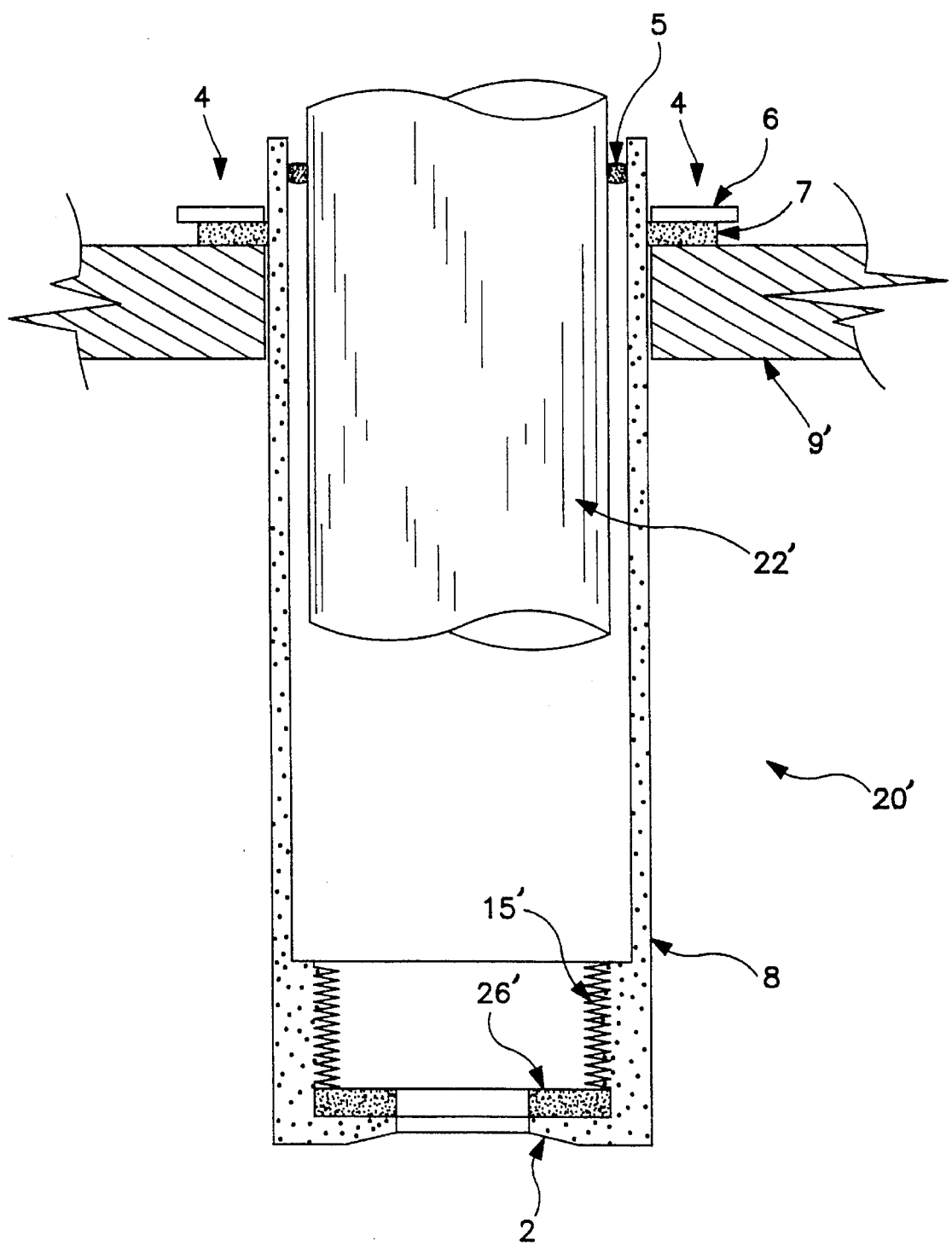
FIG. 4 is a view, partly in section and partly in projection, with the part in projection partially broken away, of an alternative preferred embodiment in which a rigid shield body is provided in a single piece.

An alternative design 20' incorporating a particularly easily retrofittable shield means is depicted in FIG. 4, which shows only the middle part of container wall 22' in projection; the lower part of container wall 22' and the interior thereof in this embodiment have features depicted in FIG. 2b, which is the same as FIG. 2a except that the reference numbers are primed, to indicate that they apply to alternative 20', and the upper part of container wall 22' is connected to at least components 10 and 11 as shown in FIG. 1 and to features interior thereto, as generally described above and well known in the art. Single piece rigid shield element 8 has a circular hole at the bottom thereof, surrounded by a projection 2 which is an integral part of shield 8 and provides a restraining surface for lower gasket 26'. The upper part of shield 8 has an inside diameter sufficiently large that container wall 22' can slide freely within it. This hollow space within the shield is connected with the circular hole in the bottom of the shield by a transition zone consisting of an upper part with a zone that is grossly cylindrical but with threaded interior walls 15' and a lower part that is cylindrical with smooth walls for a distance at least long enough to accommodate lower gasket 26'. During assembly or retrofitting, shield 8 with the lower gasket already in place therein is screwed over the lower end of container wall 22', with its threaded portion 16' that mates with threaded walls 15' in shield 8, until the lower gasket 28' is compressed against both the lower retaining surface in the bottom of the shield wall and the solid fluoride(s) membrane 24', the flat bottom surface 33' of container wall 18', and set cement ring 3', the latter being covered completely, so that it is protected from contact with the liquid composition in which the free fluoride ions concentration is to be measured.

Shield 8 is sufficiently long to extend through mounting block 9' and may be fixed therein in any convenient manner, one example of which is shown in the upper part of FIG. 4. An upper O-ring 5 fits between container wall 22' and the interior cylindrical wall of shield 8 to serve as a centering device, stabilize mechanically the assembly of elements 22' and 8, which otherwise would be joined only near their lower end, and permit the distance between the walls of elements 22' and 8 to vary as required to accommodate differential thermal expansion and contraction. The assembly of elements 22' and 8' is held in mounting block 9' by means of an intermediate gasket 7 and upper collar 6, which is urged against intermediate gasket 7 by a mechanical force represented by arrows 4, so that gasket 7 is compressed against the exterior wall of shield 8 sufficiently firmly to (i) prevent the latter from sliding downward, under the influence of ambient gravity, through the hole in mounting block 9' through which shield 8 passes and (ii) provide a liquid tight seal to prevent the liquid in which the free fluoride ions concentration is to be measured from moving into the dry end of the assembly past upper collar 6, which can not itself be tightly sealed against rigid shield element 22 in this design. The mechanical force could be provided by a spring, screw, lever, piston, or any like device.

A combination of a shield such as shield 8 in FIG. 4 and an elastomeric gasket such as gasket 26' shown in FIG. 4 is, like the alternative described in FIG. 1, well suited to provide a retrofittable shield according to this invention for certain models of current commercial free fluoride ion sensitive electrodes, which often include at least elements 3, 33, 24, 30, 32, 22, 10, and 11 as shown and described above. If the lower end of container wall 22 is not already threaded, it can easily be threaded by a retrofitter, and then converted into an electrode apparatus according to this invention by screwing a combination of elements 8 and 26' as shown in FIG. 4 over the threaded end of the container wall of the commercially supplied free fluoride ion sensitive electrode. If it is desired to mount the free fluoride ion sensitive electrode as so modified in a mounting block already provided with a hole to accommodate a normal size commercial electrode, this can usually be easily accomplished by simply widening the hole enough to accommodate the modified electrode assembly.

Although annular body 3 in FIGS. 2a and 2b is normally a completely set, originally slow-setting cement as noted above in current commercially available electrodes, it can also be an elastomer body with the same shape and placement as described above for the set cement ring. Such an elastomer ring is preferably and suitably made from the same materials as specified for other elastomeric components above. Also, as already briefly noted above, any retaining surface specified as flat above instead may have a narrow annular projection on an otherwise flat surface, as illustrated in FIG. 3a. Such a projection focuses the compressive force applied to seal the elastomer body pressed against the retaining surface into a smaller volume of the elastomer body and thus allows adequately tight sealing at smaller overall pressures. A corresponding groove, at least slightly shallower than the projection over which it is to fit, can also be molded into the elastomer body as an alignment aid.

What is claimed is:

1. A free fluoride ion sensitive electrode, comprising:

(A) a substantially liquid impermeable membrane that is constituted of one or more fluoride ion-sensitive solid, crystalline, substantially water insoluble fluorides;

(B) a container with walls that are electrically insulating, except in a portion of the walls that is constituted exclusively of membrane component (A), with one side of said membrane component on the exterior and the other side of said membrane component on the interior of the container, the walls of the container enclosing a substantially liquid- and vapor-tight space;

(C) a volume of a first liquid ionic solution of known composition and concentration confined within the substantially liquid- and vapor-tight space within container component (B) and in physical contact with the interior surface of membrane component (A);

(D) a first reference electrode enclosed within the substantially liquid- and vapor-tight space within container component (B), said first reference electrode including a metallic electrical conductor that is in physical contact with ionic solution component (C) but is not in physical contact with membrane component ( A );

(E) an electrically conducting lead component that is in physical contact with both the metallic electrical conductor part of reference electrode component (D) and a point outside the substantially liquid- and vapor-tight space within container component (B) but is not in physical contact with membrane component (A) or with component (C); and (F) shield means including an exterior surface that prevents any substantial physical contact between (i) any liquid composition in which the concentration of free fluoride ions is to be measured with the aid of the free fluoride ion sensitive electrode and (ii) any part of the exterior wall of container component (B) other than a part of said exterior wall which is constituted exclusively by one side of membrane component (A), while allowing physical contact between (i) any liquid composition in which the concentration of free fluoride ions is to be measured with the aid of the free fluoride ion sensitive electrode and (ii) at least pad of the exterior surface of membrane component (A).

2. A free fluoride ion sensitive electrode according to claim 1, wherein:

(I) the exterior walls of container component (B) comprise an elongated section connected on one end thereof to a working end section, and the working end section comprises (i) a central portion that is constituted entirely of exterior surface of membrane component (A), (ii) in exterior portion that is integral with the nearest parts of the elongated lateral section of container component (B), and (iii) an intermediate portion that is the exterior part of a volume of completely set, originally slow-setting, cement that bonds membrane component (A) to the exterior portion of the working end section; and (II) the shield means (F) comprise:

(II.1) a primary elastomeric shield body having a central hole therethrough;

(II.2) a rigid shield body, which may be either a single piece or a subassembly of a plurality of rigid shield elements connected by gasketing or adhesive, said rigid shield body covering all otherwise uncovered parts of the walls of container component (B) except for at least one part thereof which is constituted exclusively of said central portion of said working end section of container component (B); said rigid shield body also having on one end thereof an interior retaining surface including a hole therethrough, said interior retaining surface having a size and shape that retains said primary elastomeric shield body when pressed thereagainst; and (II.3) means for maintaining alignment among the primary elastomeric shield body, the interior retaining surface of the rigid shield body, and the working end section of the exterior walls of container component (B) and for maintaining compressive force between the interior retaining surface of the rigid shield body and the working end section of the exterior walls of container component (B), without causing mechanical damage to any part of any of components (A) through (E), to form from the rigid shield body, the primary elastomeric shield body, and the container component (B) an assembly in which (i) the primary elastomeric shield body is between the interior retaining surface of the rigid shield body and the working end section of the exterior walls of container component (B) and is compressed to form a sealing contact, between the primary elastomeric shield body and a part of each of the interior retaining surface of the rigid shield body and the working end section of the exterior walls of container component (B), so that (i) the sealing contact prevents any flow of liquid, between the primary elastomeric shield body and either of the interior retaining surface of the rigid shield body or the working end section of the exterior walls of container (B), to a point where the liquid would contact any part of the exterior walls of container component (B) which is not constituted exclusively of exterior surface of membrane component (A); (ii) any area of said working end section of container component (B) that is interior to the sealing contact formed thereagainst by the primary elastomeric shield body consists exclusively of exterior surface of membrane component (A); and (iii) there exists at least a part of the exterior surface of membrane component (A) in the working end section of container component (B) that is not prevented by any part of the shield means from making physical contact with any liquid with which any portion of the assembly of the rigid shield body, the primary elastomeric shield body, and container component (B) that includes said working end section of container component (B) is brought into contact.

3. A free fluoride ion sensitive electrode according to claim 2, wherein: (i) component (B) end the shield body have shapes that are substantially those of hollow cylinders and have lateral exterior and interior substantially cylindrical surfaces that are longer than the diameter of their substantially flat end surfaces; (ii) the interior retaining surface of the shield body is a substantially flat annular disk; (iii) the primary elastomeric shield body is a fluorocarbon elastomer gasket; and (iv) the means for maintaining alignment and compressive force comprise (iv.1) male screw threads on a threaded zone of the lateral substantially cylindrical exterior wall of container component (B), this threaded zone extending to the end of said exterior wall adjacent to the working end section of the exterior wall, (iv.2) a substantially cylindrical unthreaded zone of the interior lateral substantially cylindrical surface of a single piece rigid shield body, or of a terminal rigid shield element of a rigid shield body subassembly, immediately adjacent to the interior retaining surface thereof; (iv.3) a cylindrical volume, of which said substantially cylindrical unthreaded zone forms the outer lateral walls, within the rigid shield body, this cylindrical volume being wide and long enough to accommodate the fluorocarbon elastomer gasket in an uncompressed condition, (iv.4) a substantially cylindrical female threaded zone of the interior lateral substantially cylindrical surface of the single rigid shield body or terminal rigid shield element of the shield body subassembly, immediately adjacent to the unthreaded zone recited in part (iv.2) on the opposite side thereof from the interior retaining surface, said female threaded zone mating with the male screw threads recited in part (iv.1) and having an inside diameter smaller than the outside diameter of the fluorocarbon elastomer gasket in its uncompressed state; (v) the fluorocarbon elastomer gasket is compressed, without causing mechanical damage to any other part of any of components (A) through (F), by mating some or all of the female threaded zone of the interior lateral substantially cylindrical surface of the single rigid shield body or terminal rigid shield element of a shield body subassembly, while the fluorocarbon elastomer gasket is in place between the female threaded zone and the interior retaining surface, with some or all of the male screw threads recited in part (iv.1), to form a sealing contact between said fluorocarbon elastomer gasket and a portion of each of said interior retaining surface and said working end section of the exterior walls of container component (B) that will prevent any flow of liquid, between (v.1) said primary elastomeric shield body and (v.2) either of (v.2.1) said interior retaining surface of the single rigid shield body or terminal rigid shield element a shield body subassembly or (v.2.2) said working end section of the exterior walls of container (B), to a point where the liquid contacts any part of the exterior walls of container component (B) which is not constituted exclusively of exterior surface of membrane component (A).

4. A free fluoride ion sensitive electrode according to claim 3, wherein:

(i) the rigid shield body is a subassembly of at least two rigid shield elements and at least one elastomeric gasket in addition to the above-recited primary elastomeric shield body; (ii) one of the rigid shield elements is a terminal collar element comprising the elements recited in parts (iv.2) and (iv.3) of claim 3; (iii) all of the rigid shield elements except the collar are hollow cylinders with an inside diameter sufficiently large that they can pass freely over the outer lateral walls of container component (B) and have both internal end external lateral surfaces that are substantially cylindrical in shape, except that one end of the external lateral surface of a rigid shield element other than the collar element which includes an end among all ends of all rigid shield elements other than the collar that is farthest from the collar when the collar and all the other rigid shield elements are assembled into the shield body subassembly for use, has a zone of male screw threads thereon; (iv) the free fluoride ion sensitive electrode is mounted on and through a solid mounting block having boundaries including two substantially flat and parallel surfaces, said mounting block having a substantially cylindrical hole therethrough that is bounded by a substantially cylindrical lateral interior surface of the mounting block and has a sufficiently large diameter that the end of the elongated portion of the exterior walls of container component (B) opposite the working end section thereof can slide freely through said hole through the mounting block; (v) the lateral internal surface of the mounting block that bounds said hole through the mounting block has, on the end thereof that is nearer to the shield body when assembled, a female threaded zone that mates when assembled with the zone of male screw threads recited in part (iii); (vi) the elongated portion of the exterior walls of container element (B) is sufficiently long to extend through the entire thickness of the mounting block when assembled, and is rigidly attached, on the side of the mounting block opposite the rigid shield subassembly, to a projection sufficiently large in size that the projection can not pass through the hole in the mounting block through which the elongated portion of the exterior walls of container element (B) passes; (vii) means for exerting a compressive force between the projection recited in part (vi) and the flat surface of the mounting block nearer to said projection are present; (viii) an elastomeric gasket is present between (viii.1) the end of the terminal collar rigid shield element farther from the internal retaining surface therein and (viii.2) the nearer or nearest of the other rigid shield element or elements and an elastomeric gasket is also present between each additional end, other than the end having a zone of male screw threads thereon, of any rigid shield element other then the collar element and the nearer or nearest end of another distinct rigid shield element other than the collar element; (ix) each of the gaskets recited in part (viii) above has a hole therethrough, this hole being large enough that the cylindrical exterior walls of container component (B) can slide freely therethrough, and when compressed forms a sealing interface, so that no liquid can flow through the interface between the gasket and the surface of either rigid shield element with which the gasket is in contact to a point where such liquid contacts any part of the exterior walls of container component (B) that is not constitute exclusively of exterior surface of membrane component (A); (x) a part of the female threaded zone on the interior of the terminal collar rigid shield element is mated, while the fluorocarbon elastomer gasket that constitutes the primary elastomeric shield body is in place between the female threaded zone of the collar and the interior retaining surface of the collar, with some or all of the male screw threads recited in part (iv.1) of claim 3, without causing mechanical damage to any part of any of components (A) through (F), to form a sealing contact between said fluorocarbon elastomer gasket and a portion of each of the interior staining surface of the collar and the working end section of the exterior walls of container component (B) that will prevent any flow of liquid between said fluorocarbon elastomer gasket and either of said interior retaining surface of said shield body or said working end section of the exterior walls of container (B) to contact any part of the exterior walls of container component (B) which is not constituted exclusively of exterior surface of membrane component (A); and (xi) a compressive force is applied between (xi.1) the projection attached to the part of the elongated exterior surface of the walls of container component (B) farther from the exterior surface of membrane component (A) and (xi.2) the nearer flat surface of the mounting block, said compressive force compressing each gasket as recited in part (viii) above, without causing any mechanical damage to any part of the free fluoride ion sensitive electrode or the mounting block, so that no liquid can flow through an interface, between the gasket and either rigid shield element with which the gasket is in contact, to contact any part of container element (B) that is not constituted exclusively of exterior surface of membrane component (F).

5. A free fluoride ion sensitive electrode according to claim 4, wherein the compressive force is provided by a coil spring.

6. A free fluoride ion sensitive electrode according to claim 4, wherein:

(i) the nonlateral surface of the rigid shield element that is adjacent to the lateral surface of the rigid shield element that has male threads thereon is substantially flat; (ii) the hole through the mounting block through which the elongated exterior wall of container component (B) passes includes an unthreaded cylindrical zone adjacent to its female threaded zone and a substantially flat retaining surface adjacent to said unthreaded cylindrical zone on the end thereof opposite the female threaded zone; and (iii) an upper fluorocarbon elastomer gasket is present in the space bounded by the cylindrical walls of said unthreaded cylindrical zone, said flat nonlateral surface of the rigid shield element, and the substantially flat retaining surface in the hole in the mounting block through which the elongated exterior wall of container component (B) passes, so that the upper fluorocarbon elastomer gasket will be compressed along with the gaskets recited in claim 4, the upper fluorocarbon elastomer gasket having (iii.1) an inside diameter through which the elongated portion of the exterior wall of container component (B) can slide freely and (iii,2) when compressed by the same compressive force used to compress the gaskets recited in part (vii) of claim 4 forms a seal, between itself end each rigid surface with which it is in contact, so that no liquid can flow through the seal to a point where such liquid would contact any part of the exterior walls of container component (B) that is not constituted exclusively of exterior surface of membrane component (A).

7. A free fluoride ion sensitive electrode according to claim 6, wherein the compressive force is provided by a coil spring.

8. A process comprising steps of (i) monitoring the free fluoride ions concentration of a process solution as the process solution is used by measuring the voltage developed between a free fluoride ion sensitive electrode and a second reference electrode and (ii) adjusting the free fluoride ions concentration of the process solution to maintain said concentration between set limits, wherein the improvement comprises using as the free fluoride ion sensitive electrode an electrode according to claim 7.

9. A free fluoride ion sensitive electrode according to claim 3, wherein:

(i) the shield body comprises a single rigid shield element having exterior walls that include two nonlateral end portions and an elongated lateral cylindrical portion; (ii) the free fluoride ion sensitive electrode is mounted on and through a solid mounting block having (ii.1) a hole therethrough with a sufficient inside diameter that the elongated cylindrical lateral exterior wall of the single rigid shield element can slide freely therethrough and (ii.2) two substantially flat and parallel boundary surfaces; (iii) the elongated cylindrical lateral exterior wall of the single rigid shield element extends on both sides of the above recited hole in the mounting block; (iv) an annular second elastomeric body (iv.1) is present on the flat surface of the mounting block that is farther from the exterior surface of membrane component (A) and (iv.2) surrounds a zone of the elongated cylindrical lateral exterior wall of the single rigid shield element that projects away from the flat surface of the mounting block that is farther from the exterior surface of membrane component (A), said annular second elastomeric body having an inside diameter sufficiently large that the elongated cylindrical lateral exterior wall of the single rigid shield element can slide freely therethrough; (v) a rigid annular compression collar is present in contact with the second elastomeric body on the side thereof opposite the mounting block; (vi) means for exerting compressive force between the compression collar and the nearer thereto of the flat surfaces of the mounting block are present and exert a compression force that is not large enough to cause mechanical damage to any part of the free fluoride ion sensitive electrode or the mounting block but that forms a sealing contact that prevents any flow of liquid between said second elastomeric body and the elongated cylindrical lateral exterior wall of the single rigid shield element to a point where the liquid contacts any part of the exterior walls of container component (B) which is not constituted exclusively of exterior surface of membrane component (A); and, optionally, (vii) a spacer ring is present between the exterior walls of container component (B) and the inner walls of the single rigid shield element at a point in space distant from the mating screw contact surfaces of the exterior walls of container component (B) and the inner walls of the single rigid shield element, to maintain the exterior walls of container component (B) and the inner walls of the single rigid shield element in substantially parallel alignment.

10. A free fluoride ion sensitive electrode according to claim 9, wherein a spacer ring as recited in part (ix) of claim 9 is present, is elastomeric, and forms a seal between itself and both the exterior walls of container component (B) end the inner walls of the single rigid shield element, to prevent any flow of liquid, between said spacer ring and either the elongated cylindrical lateral exterior wall of the single rigid shield element or the cylindrical outer lateral surface of the exterior wall of container component (B), to a point where the liquid contacts any part of the exterior walls of container component (B) which is not constituted exclusively of exterior surface of membrane component (A).

11. A process comprising steps of (i) monitoring the free fluoride ions concentration of a process solution as the process solution is used by measuring the voltage developed between a free fluoride ion sensitive electrode and a second reference electrode and (ii) adjusting the free fluoride ions concentration of the process solution to maintain said concentration between set limits, wherein the improvement comprises using as the free fluoride ion sensitive electrode an electrode according to claim 10.

12. A process comprising steps of (i) monitoring the free fluoride ions concentration of a process solution as the process solution is used by measuring the voltage developed between a free fluoride ion sensitive electrode end a second reference electrode and (ii) adjusting the free fluoride ions concentration of the process solution to maintain said concentration between set limits, wherein the improvement comprises using as the free fluoride ion sensitive electrode an electrode according to claim 2.

13. A process comprising steps of (i) monitoring the free fluoride ions concentration of a process solution as the process solution is used by measuring the voltage developed between a free fluoride ion sensitive electrode and a second reference electrode and (ii) adjusting the free fluoride ions concentration of the process solution to maintain said concentration between set limits, wherein the improvement comprises using as the free fluoride ion sensitive electrode an electrode according to claim 1.

14. A retrofittable shield means for a conventional free fluoride ion sensitive electrode, said conventional free fluoride ion sensitive electrode comprising:

(A) a substantially liquid impermeable membrane that is constituted of one or more fluoride ion-sensitive solid crystalline fluorides;

(B) a container with walls that are electrically Insulating, except in at least one portion of the walls that is constituted exclusively of membrane component (A), with one side of said membrane component on the exterior and the other side of said membrane component on the interior of the container, the walls of the container enclosing a substantially liquid- and vapor-tight space; the walls of container component (B) comprising on their exterior an elongated section connected on one end thereof to a working end section that comprises (i) a central portion that is the exterior side of membrane component (A) (ii) an exterior portion that is integral with the nearest parts of the walls of container component (B) that form the part of the elongated section thereof adjacent to said working end section, and (iii) an intermediate portion that is the exterior part of an annular body of completely set, originally slow-setting cement that bonds membrane component (A) to the exterior part of the working end section that is integral with the nearest parts of the wall of container component (B) that are part of the elongated section thereof;

(C) a volume of a first liquid ionic solution of known composition and concentration confined within the substantially liquid- and vapor-tight space within container component (B) and in physical contact with the interior surface of membrane component (A);

(D) a first reference electrode enclosed within the substantially liquid- and vapor-tight space within container component (B), said first reference electrode including a metallic electrical conductor that is in physical contact with ionic solution component (C) but not in physical contact with membrane component (A); and (E) an electrically conducting lead component that is in physical contact with both the metallic electrical conductor part of reference electrode component (D) and a point outside the substantially liquid- and vapor-tight space within container component (B), but not in physical contact with component (A) or (C); said shield means comprising:

(1) a primary elastomeric shield body having a central hole therethrough;

(2) a rigid shield body, which may be either a single piece or a subassembly of a plurality of rigid shield elements connected by gasketing or adhesive said rigid shield body when in place on the electrode to be retrofitted covering all otherwise uncovered parts of the walls of container component (B) except for at least one part thereof which is constituted exclusively of said central portion of said working end section of container component (B); said rigid shield body also having on one end thereof an interior retaining surface including a hole therethrough, said interior retaining surface having a size and a shape that retains said primary elastomeric shield body when pressed thereagainst; and (3) means for maintaining alignment among the primary elastomeric shield body, the interior retaining surface of the rigid shield body, end the working end section of the exterior walls of container component (B) end for maintaining compressive force between the interior retaining surface of the rigid shield body end the working end section of the exterior walls of container component (B), without causing mechanical damage to any part of any of components (A) through (E), to form from the rigid shield body, the primary elastomeric shield body, and the container component (B) and assembly in which (i) the primary elastomeric shield body is between the interior retaining surface of the rigid shield body end the working and section of the exterior walls of container component (B) end is compressed to form a sealing contact, between the primary elastomeric shield body and a portion of each of the interior retaining surface of the rigid shield body and the working end section of the exterior walls of container component (B), so that (i) the sealing contact prevents any flow of liquid, between the primary elastomeric shield body end either of the interior retaining surface of the rigid shield body or the working end section of the exterior walls of container (B), to a point where the liquid would contact any part of the exterior walls of container component (B) which is not constituted exclusively of exterior surface of membrane component (A); (ii) any area of said working end section of container component (B) that is interior to the sealing contact formed thereagainst by the primary elastomeric shield body consists exclusively of exterior surface of membrane component (A); and (iii) there exists at least a part of the exterior surface of membrane component (A) in the working end section of container component (B) that is not prevented by any part of the shield means from making physical contact with any liquid with which any portion of the assembly of the rigid shield body, the primary elastomeric shield body, and container component (B) that includes said working end section of container component (B) is brought into contact.

15. A retrofittable shield according to claim 14 for a conventional free fluoride ion sensitive electrode having a container component (B) with (1) a shape that is substantially that of a hollow cylinder having lateral exterior and interior substantially cylindrical surfaces that are longer then the diameter of their substantially flat end surfaces: (2) a working end section that is a substantially flat circular disk: and (3) male screw threads on a threaded zone of its exterior lateral wall, said threaded zone extending to the end of the exterior lateral wall adjacent to the working end section of the exterior wall, wherein: (i) the shape of the rigid shield body is substantially that of a hollow cylinder and has lateral exterior and interior substantially cylindrical surfaces that are longer than the diameter of its substantially flat end surfaces; (ii) the interior retaining surface of the shield body is a substantially flat annular disk; (iii) the primary elastomeric shield body is a fluorocarbon elastomer gasket; (iv) the means for maintaining alignment and compressive force comprise (iv.1) a substantially cylindrical unthreaded zone of the interior lateral substantially cylindrical surface of a single piece rigid shield body, or of a terminal rigid shield element of a rigid shield body subassembly, immediately adjacent to the interior retaining surface thereof; (iv.2) a cylindrical volume, of which said substantially cylindrical unthreaded zone forms the outer lateral walls, within the rigid shield body, this cylindrical volume being wide and long enough to accommodate the fluorocarbon elastomer gasket in an uncompressed condition, (iv.3) a substantially cylindrical female threaded zone of the interior lateral substantially cylindrical surface of a single rigid shield body, or of a terminal rigid shield element of a shield body subassembly immediately adjacent to the unthreaded zone recited in part (iv.1) on the opposite side thereof from the interior retaining surface, said female threaded zone mating with the male screw threads recited in part (iv.1) when the shield is put into place on an electrode to be retrofitted and having an inside diameter smaller than the outside diameter of the fluorocarbon elastomer gasket in its uncompressed state; (v) the compressibility of the fluorocarbon elastomer gasket and the relative sizes of the fluorocarbon elastomer gasket and of the elements recited in parts (iv.1) through (iv.3) are such that the fluorocarbon elastomer gasket is compressed, without causing mechanical damage to any other part of any of components (A) through (F), by mating some or all of the female threaded zone of the interior lateral substantially cylindrical surface of the single rigid shield body or a terminal rigid shield element of a shield body subassembly, while the fluorocarbon elastomer gasket is in place between the female threaded zone and the interior retaining surface, with some or all of the male screw threads in the threaded zone of the lateral substantially cylindrical exterior wall of container component (B), to form a sealing contact that prevents any flow of liquid, between (v.1) said primary elastomeric shield body and (v.2) either of (v.2.1) said interior retaining surface of the rigid shield body or a terminal element of shield body subassembly or (v.2.2) said working end section of the exterior walls of container (B), to a point where the liquid contacts any part of the exterior walls of container component (B) which is not constituted exclusively of exterior surface of membrane component (A).

16. A retrofittable shield body according to claim 15 for a conventional free fluoride electrode that is mounted on and through a solid mounting block having boundaries including two substantially flat end parallel surfaces, said mounting block having a substantially cylindrical hole therethrough that is bounded by a substantially cylindrical lateral interior surface of the mounting block and has a sufficiently large diameter that the end of the elongated portion of the exterior walls of container component (B) opposite the working end section thereof can slide freely through said hole through the mounting block, the lateral internal surface of the mounting block that bounds said hole through the mounting block having, on the end thereof that is nearer to the shield body when assembled, a female threaded zone, the elongate portion of the exterior walls of container element (B) being sufficiently long to extend through the entire thickness of the mounting block when assembled and being rigidly attached, on the side of the mounting block opposite the rigid shield body, to a projection sufficiently large in size that the projection can not pass through the hole in the mounting block through which the elongated portion of the exterior walls of container element (B) passes, means being present for exerting a compressive force between said projection attached to container element (B) and the flat surface of the mounting block nearer to said projection, wherein: (i) the rigid shield body is a subassembly of at least two rigid shield elements and at least one elastomeric gasket in addition to the above-recited primary elastomeric shield body; (ii) one of the rigid shield elements is a collar comprising the elements recited in parts (iv,2) and (iv.3) of claim 15; (iii) all of the rigid shield elements except the collar are hollow cylinders with an inside diameter sufficiently large that they can pass freely over the outer lateral walls of container component (B) and have both internal and external lateral surfaces that are substantially cylindrical in shape, except that one end of the exterior surface of a rigid shield element other then the collar which includes the end among all ends of all the rigid shield elements other than the collar that is farthest from the collar when the collar and all the other rigid shield elements are assembled into the shield body subassembly for use, has a zone of male screw threads thereon that mates with the female screw threads on the lateral internal surface of said hole through the mounting block (iv) an elastomeric gasket is present between (iv.1) the end of the collar farther from the internal retaining surface therein and (iv.2) the nearer end of the nearer or nearest of the other rigid shield element or elements and an elastomeric gasket is also present between any additional end, other than the end having a zone of male screw threads thereon, of a rigid shield element other than the collar and the nearer or nearest end of another distinct rigid shield element other than the collar; (v) each of the gaskets recited in part (iv) above has a hole therethrough, this hole being large enough that the cylindrical exterior walls of container component (B) can slide freely therethrough; (vi) when the shield is in place on an electrode to be retrofitted, a part of the female threaded zone on the interior of the collar is mated, while the fluorocarbon elastomer gasket is in place between the female threaded zone of the collar and the interior retaining surface of the collar, with some or all of the male screw threads on the exterior lateral surface of container element (B), without causing mechanical damage to any part of any of components (A) through (F), to form a sealing contact that prevents any flow of liquid between said primary elastomeric shield body and either of said interior retaining surface of said shield body or said working end section of the exterior walls of container (B) to a point where the liquid contacts any part of the exterior walls of container component (B) which is not constituted exclusively of exterior surface of membrane component (A); and (viii) when the shield is put, into place, a compressive force is applied between (viii.1) the projection attached to the part of the elongated exterior surface of the walls of container component (B) farther from the exterior surface of membrane component (A) and (vii.2) the nearer flat surface of the mounting block, said compressive force being sufficient to compress each gasket recited in part (iv) above so that no liquid can flow, between the gasket and the surface of either rigid shield element with which the gasket is in contact, to contact any part of the exterior walls of container competent (B) that is not constituted exclusively of exterior surface of membrane component (A) end insufficient to cause any mechanical damage to any part of the free fluoride ion sensitive electrode or the mounting block.

17. A retrofittable shield means according to claim 16, wherein the compressive force is provided by a coil spring.

18. A retrofittable shield means according to claim 16 for a fluoride sensitive electrode mounted in a mounting block in which the hole therethrough through which the elongated exterior wall of container component (B) passes includes an unthreaded cylindrical zone adjacent to its female threaded zone and a substantially flat retaining surface adjacent to said unthreaded cylindrical zone on the end thereof opposite the female threaded zone, wherein: (i) the nonlateral surface of the rigid shield element that is adjacent to the lateral surface of the rigid shield element that has male threads thereon is substantially flat and (ii) an upper fluorocarbon elastomer gasket is present in the space bounded by the cylindrical walls of said unthreaded cylindrical zone, said flat nonlateral surface of the rigid shield element, and the substantially flat retaining surface in the hole in the mounting block through which the elongated exterior wall of container component (B) passes, so that the upper gasket will be compressed along with the gaskets recited in part (iv) of claim 16, the upper fluorocarbon elastomer gasket having (ii.1) an inside diameter through which the elongated portion of the exterior wall of container component (B) can slide freely and (ii.2) an external size, external surface shape, and elastomeric properties such that the gasket when compressed by the same compressive force as recited in part (viii) of claim 16, forms a seal, so that no liquid can flow between the gasket and either said retaining surface or said nonlateral flat surface of the rigid shield element adjacent to the lateral surface thereof having male threads thereon to contact any part of the exterior walls of container component (B) that is not constituted exclusively of exterior surface of membrane component (A).

19. A retrofittable shield means according to claim 15 for a free fluoride ion sensitive electrode that is mounted and through solid mounting block having both (a) a hole therethrough with a sufficient inside diameter that the elongated cylindrical lateral exterior surface of the single rigid shield element can slide freely therethrough and (b) two substantially flat and parallel boundary surfaces, wherein (i) the shield body comprises a single rigid shield element having exterior walls that include two nonlateral end portions and an elongated lateral cylindrical portion; (ii) the elongated cylindrical lateral exterior wall of the single rigid shield element extends on both sides of the above recited hole in the mounting block; (iii) an annular second elastomeric body (iii.1) is present on the flat surface of the mounting block that is farther from the exterior surface of membrane component (A) and (iii.2) surrounds a zone of the elongated cylindrical lateral exterior wall of the single rigid shield element that projects away from the flat surface of the mounting block that is farther from the exterior surface of membrane component (A), said annular second elastomeric body having an inside diameter sufficiently large that the elongated cylindrical lateral exterior wall of the single rigid shield element can slide freely therethrough; (iv) a rigid annular compression collar is present in contact with the second elastomeric body on the side thereof opposite the mounting block; (v) means for exerting compressive force between the compression collar and the nearer thereto of the flat surfaces of the mounting block are present; (vi) the compressibility of the second elastomeric body and the relative sizes of the second elastomeric body and of the elongated cylindrical lateral exterior wall of the single rigid shield element are such that the second elastomeric body is compressed by the compression means recited in part (v), when the shield is put into place on the free fluoride ion sensitive electrode to be retrofitted, by a compression force that is not large enough to cause mechanical damage to any part of the free fluoride ion sensitive electrode or the mounting block, to form a seal that prevents any flow of liquid between said second elastomeric body and the elongated cylindrical lateral exterior wall of the single rigid shield element, to contact any part of the exterior walls of container component (B) which is not constituted exclusively of exterior surface of membrane component (A); and, optionally, (vii) a spacer ring is present between the exterior walls of container component (B) and the inner walls of the single rigid shield element at a point in space distant from the mating screw contact surfaces of the exterior walls of container component (B) and the inner walls of the single rigid shield element, to maintain the exterior walls of container component (B) end the inner walls of the single rigid shield element in substantially parallel alignment.

20. A retrofittable shield means according to claim 19, wherein a spacer ring as recited in part (vii) of claim 19 is present and forms a seal between itself and both the exterior walls of container component (B) and the inner walls of the single rigid shield element, to prevent any flow of liquid, between said spacer and either the elongated cylindrical lateral exterior wall of the single rigid shield element or the cylindrical outer lateral surface of the exterior wall of container component (B), to contact any part of the exterior walls of container component (B) which is not constituted exclusively of outer surface of membrane component (A).

\* \* \* \* \*